(12) United States Patent
Tsukui et al.

(10) Patent No.: US 9,056,094 B2
(45) Date of Patent: Jun. 16, 2015

(54) ADJUVANT

(75) Inventors: Toshihiro Tsukui, Fukushima (JP); Ken Ishii, Osaka (JP); Shizuo Akira, Osaka (JP); Cevayir Coban, Osaka (JP)

(73) Assignees: NIPPON ZENYAKU KOGYO CO., LTD., Fukushima (JP); OSAKA UNIVERSITY, Osaka (JP)

( * ) Notice: Subject to any disclaimer, the term of this patent is extended or adjusted under 35 U.S.C. 154(b) by 719 days.

(21) Appl. No.: 12/740,899

(22) PCT Filed: Oct. 31, 2008

(86) PCT No.: PCT/JP2008/069919
§ 371 (c)(1),
(2), (4) Date: Apr. 30, 2010

(87) PCT Pub. No.: WO2009/057763
PCT Pub. Date: May 7, 2009

(65) Prior Publication Data
US 2010/0247568 A1 Sep. 30, 2010

(30) Foreign Application Priority Data
Nov. 2, 2007 (JP) .................................. 2007-285737

(51) Int. Cl.
| | |
|---|---|
| *A61K 9/00* | (2006.01) |
| *A61K 39/00* | (2006.01) |
| *A61K 39/39* | (2006.01) |
| *A61K 47/46* | (2006.01) |
| *A61K 39/35* | (2006.01) |

(52) U.S. Cl.
CPC ............... *A61K 39/39* (2013.01); *A61K 9/0019* (2013.01); *A61K 39/35* (2013.01); *A61K 47/46* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 5,846,735 A * | 12/1998 | Stapleton et al. | ............... 435/7.1 |
| 5,849,307 A | 12/1998 | Metz et al. | |
| 6,193,971 B1 * | 2/2001 | Hofmann et al. | .......... 424/191.1 |
| 6,753,417 B2 * | 6/2004 | Hansen et al. | ............... 536/23.1 |
| 2009/0041808 A1 | 2/2009 | Akira et al. | |
| 2010/0111981 A1 * | 5/2010 | Bohle et al. | ............... 424/184.1 |

FOREIGN PATENT DOCUMENTS

| | | |
|---|---|---|
| WO | 2006/061965 | 6/2006 |
| WO | 2007/147255 | 12/2007 |

OTHER PUBLICATIONS

Ulmer et al. Vaccine 18: 18-28, 2000.*
Wilcock et al. J. Allerg. Clin. Immunol. 113: S107, Feb. 2004.*
Wichman et al. Avian Diseases 18: 631-633, 1974.*
The New Riverside University Dictionary, The Riverside Publishing Company, p. 933, 1984.*
Illustrated Stedman's Medical Dictionary, 24th Edition, Williams and Wilkins, London, p. 707, 1982.*
Kashala et al. Vaccine 20: 2263-2277, 2002.*
Bernstein et al. Clin. Infect. Dis. 40: 1271-1281, May 2005.*
Cevayir Coban et al., "Purified Malaria Pigment (Hemozoin) Enhances Dendritic Cell Maturation and Modulated the Isotype of Antibodies Induced by DNA Vaccine.", Infection and Immunity, Jul. 2002 vol. 70 No. 7, Nov. 2008, pp. 3939-3943.
Ken J. Ishii et al., "Toll or Toll-Free Adjuvant Path Toward the Optimal Vaccine Development.", Journal of Clinical Immunology, vol. 27, No. 4 Jul. 2007., Mar. 2007, pp. 363-371.
Andrew F.G. Slater et al., "An Iron-Carboxylate bond links the heme units of malaria pigment.", Proc. Natl. Acad. Sci. USA vol. 88 Jan. 1991 Biochemistry., Oct. 1990, pp. 325-329.
Cevayir Coban et al., "Toll-like receptor 9 mediates innate immune activation by the malaria pigment hemozoin.", JEM The Rockefeller University Press vol. 201, No. 1, Jan. 2005, pp. 19-25.
Coban et al., "The Malarial Metabolite Hemozoin and Its Potential Use as a Vaccine Adjuvant" Allergology International, vol. 59, No. 2, pp. 115-124, 2010.
Extended European Search Report for EP Application No. 08845024. 2, dated Jan. 12, 2011.

* cited by examiner

*Primary Examiner* — S. Devi
(74) *Attorney, Agent, or Firm* — Greenblum & Bernstein, P.L.C.

(57) ABSTRACT

The present invention provides a vaccine adjuvant composition which is used in combination with an allergen vaccine, infection vaccine or tumor vaccine. The present invention specifically provides a vaccine adjuvant composition comprising hemozoin or β-hematin and being used in combination with an allergen vaccine, infection vaccine or tumor vaccine, and a vaccine composition comprising the vaccine adjuvant composition and an allergen vaccine, infection vaccine or tumor vaccine.

7 Claims, 24 Drawing Sheets

1 rDerf2 2 μg + β-hematin (1 mM) + Alum adjuvant (100 μg): 4 animals
2 rDerf2 1 μg + β-hematin (1 mM) + Alum adjuvant (100 μg): 4 animals
3 rDerf2 2 μg + Alum adjuvant (100 μg): 3 animals
4 rDerf2 1 μg + Alum adjuvant (100 μg): 4 animals 1 rDerf2 2 µg + β-hematin (1 mM) + Alum adjuvant (100 µg): 4 animals
2 rDerf2 1 µg + β-hematin (1 mM) + Alum adjuvant (100 µg): 4 animals
3 rDerf2 2 µg + Alum adjuvant (100 µg): 3 animals
4 rDerf2 1 µg + Alum adjuvant (100 µg): 4 animals 1 rDerf2 2 μg + β-hematin (1 mM) + Alum adjuvant (100 μg): 4 animals
2 rDerf2 1 μg + β-hematin (1 mM) + Alum adjuvant (100 μg): 4 animals
3 rDerf2 2 μg + Alum adjuvant (100 μg): 3 animals
4 rDerf2 1 μg + Alum adjuvant (100 μg): 4 animals 1 rDerf2 2 μg + β-hematin (1 mM) + Alum adjuvant (100 μg): 4 animals
2 rDerf2 1 μg + β-hematin (1 mM) + Alum adjuvant (100 μg): 4 animals
3 rDerf2 2 μg + Alum adjuvant (100 μg): 3 animals
4 rDerf2 1 μg + Alum adjuvant (100 μg): 4 animals

Fig. 5

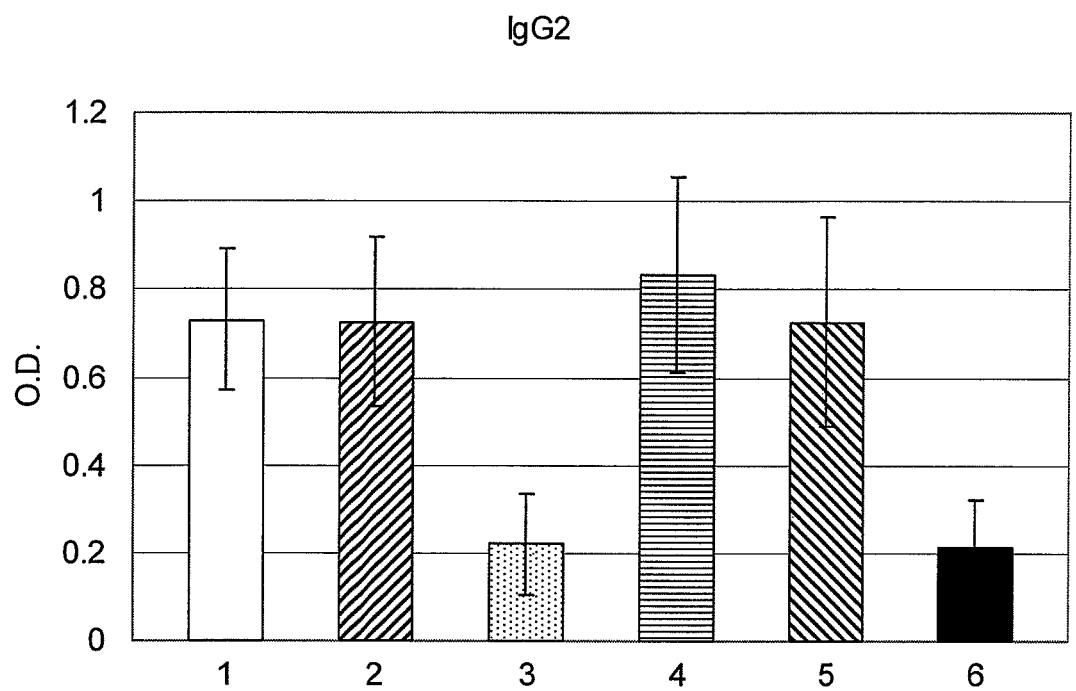

1 Collection of blood sample three weeks after administration of Derf2 100 μg + β-hematin 2 mM + Alum adjuvant 1 mg
2 Collection of blood sample three weeks after administration of Derf2 100 μg + β-hematin 1 mM + Alum adjuvant 1 mg
3 Collection of blood sample three weeks after administration of Derf2 100 μg + Alum adjuvant 1 mg
4 Collection of blood sample four weeks after administration of Derf2 100 μg + β-hematin 2 mM + Alum adjuvant 1 mg
5 Collection of blood sample four weeks after administration of Derf2 100 μg + β-hematin 1 mM + Alum adjuvant 1 mg
6 Collection of blood sample four weeks after administration of Derf2 100 μg + Alum adjuvant 1 mg ic acid, lipopolysaccharide

ADJUVANT

TECHNICAL FIELD

The present invention relates to a vaccine adjuvant composition which is to be used in combination with an allergen vaccine, an infection vaccine, a mucosal vaccine or a tumor vaccine.

BACKGROUND ART

Hemozoin is a hydrophobic hem polymer which is the detoxification product of the hem molecules found in the food vacuole of *Plasmodium* protozoa, and it can be produced by digestion of host hemoglobin by *Plasmodium* protozoa. Like CpG DNA, hemozoin acts as a ligand of Toll-like receptor 9 (TR9). It is reported that the Toll-like receptor 9 is involved in the innate immune response to various pathogens including *Plasmodium*. In other words, immune system is activated in a MyD88-dependent manner when Toll-like receptor 9 recognizes a ligand.

The hemozoin synthesized from hemin chloride is called β-hematin (see non-patent document 1).

It is reported that hemozoin activates in vitro spleen cells and dendritic cells of mice (see patent document 1). It is also reported that hemozoin has an adjuvant effect on the antibody production of ribonuclease A in mice (see patent document 2).

In addition, it is reported that β-hematin has an effect as an adjuvant of DNA vaccines (see non-patent document 2), and (see non-patent document 2), and it is further reported that β-hematin functions as a ligand other than TLR9 DNA molecules (non-methylated DNA chain that is called a so-called CpG motif) (see non-patent document 3).

However, there was no disclosure that hemozoin and β-hematin could be used as a vaccine adjuvant for potentiating in vivo effect of allergen vaccines or bacterial or viral infection vaccines.

Patent document 1: International patent publication No. WO 2006/061965 pamphlet

Patent document 2: U.S. Pat. No. 5,849,307

Non-patent document 1: Slater et al., Proc. Natl. Acad. Sci. U.S.A. 88: 325-329, 1991

Non-patent document 2: Infect. Immun. 2002 July; 70(7): 3939-43

Non-patent document 3: J Exp Med. 2005 Jan. 3; 201(1): 19-25

DISCLOSURE OF THE INVENTION

The Problem to be Solved by the Invention

An object of the present invention is to provide a vaccine adjuvant composition which is to be used in combination with an allergen vaccine, an infection vaccine, a mucosal vaccine or a tumor vaccine.

Means for Solving the Problem

The present inventors have studied earnestly on vaccine adjuvant compositions for potentiating in vivo effects of vaccines to animals. They have found that vaccine effects can be potentiated by vaccination to animals using a vaccine adjuvant composition comprising an allergen vaccine, a bacterial or viral infection vaccine, a mucosal vaccine or a tumor vaccine in combination with hemozoin or β-hematin, and completed the present invention.

Namely, the present invention is as follows.

[1] A vaccine adjuvant composition comprising hemozoin or β-hematin and being used in combination with an allergen vaccine.

[2] The vaccine adjuvant composition according to the item [1], comprising 5 μM to 2 mM of hemozoin or β-hematin.

[3] The vaccine adjuvant composition according to the item [1] or [2], which is a mucosal vaccine adjuvant.

[4] A vaccine composition comprising the vaccine adjuvant composition according to any one of the items [1] to [3] and an allergen vaccine.

[5] The vaccine composition according to the item [4], which is a mucosal vaccine.

[6] The vaccine composition according to the item [4] or [5], wherein the allergen is a pollen allergen or a mite allergen.

[7] A vaccine adjuvant composition which is to be used in combination with an infection vaccine comprising hemozoin or β-hematin.

[8] The vaccine adjuvant composition according to the item [7], comprising 5 μM to 2 mM of hemozoin or β-hematin.

[9] The vaccine adjuvant composition according to the item [7] or [8], which is a mucosal vaccine adjuvant.

[10] A vaccine composition comprising the vaccine adjuvant composition according to any one of the items [7] to [9] and an infection vaccine.

[11] The vaccine composition according to the item [10], which is a mucosal vaccine.

[12] A vaccine composition according to the item [10] or [11], wherein the infection is an infection due to bacteria or viruses.

[13] A vaccine adjuvant composition which is to be used in combination with a tumor vaccine comprising hemozoin or β-hematin.

[14] The vaccine adjuvant composition according to the item [13], comprising 5 μM to 2 mM of hemozoin or β-hematin.

[15] The vaccine adjuvant composition according to the item [13] or [14], which is a mucosal vaccine adjuvant.

[16] A vaccine composition comprising the vaccine adjuvant composition according to any one of the items [13] to [15] and a tumor vaccine.

[17] The vaccine composition according to the item [16], which is a mucosal vaccine.

[18] A dendritic cell activator comprising hemozoin or β-hematin.

[19] The dendritic cell activator according to the item [18], comprising 5 μM to 2 mM of hemozoin or β-hematin.

[20] A vaccine adjuvant composition comprising hemozoin or β-hematin and Alum adjuvant.

[21] The vaccine adjuvant composition according to the item 20, which induces Th1 immunoreaction.

[22] The vaccine adjuvant composition according to the item [20] or [21], which is a mucosal vaccine.

[23] A vaccine composition comprising the vaccine adjuvant composition according to any one of the items [20] to [22] and a vaccine.

[24] The vaccine composition according to the item [23], which is a mucosal vaccine.

Effect of the Invention

When the vaccine adjuvant composition of the present invention comprising hemozoin or β-hematin is used in combination with an allergen vaccine or an infection vaccine for pathogens such as bacteria, viruses, rickettsiae, parasites, and the like, the antibody titer for such pathogens is elevated in vivo, and allergic diseases and infectious diseases can be prevented or treated more effectively, compared to the case where an adjuvant is not used in combination. In addition, combination use of the vaccine adjuvant composition of the present invention comprising hemozoin or β-hematin with a mucosal vaccine can induce mucosal IgA antibody production in the mucosal membrane, and can prevent or treat the infections (infectious disease) effectively. Moreover, when the vaccine adjuvant composition of the present invention comprising hemozoin or β-hematin is used in combination with a tumor vaccine, reduction in tumor size can be observed, and thus tumor can be prevented or treated effectively.

The present specification includes the contents as disclosed in the description and/or drawings of Japanese Patent Application No. 2007-285737, which is a priority document of the present application.

BRIEF DESCRIPTION OF THE DRAWINGS

FIG. 5 is a graph showing IgG2 antibody titers in canine serum when a vaccine composition comprising β-hematin and Alum adjuvant as an adjuvant is administered to dogs.

BEST MODE FOR CARRYING OUT THE INVENTION

Figure 1A:
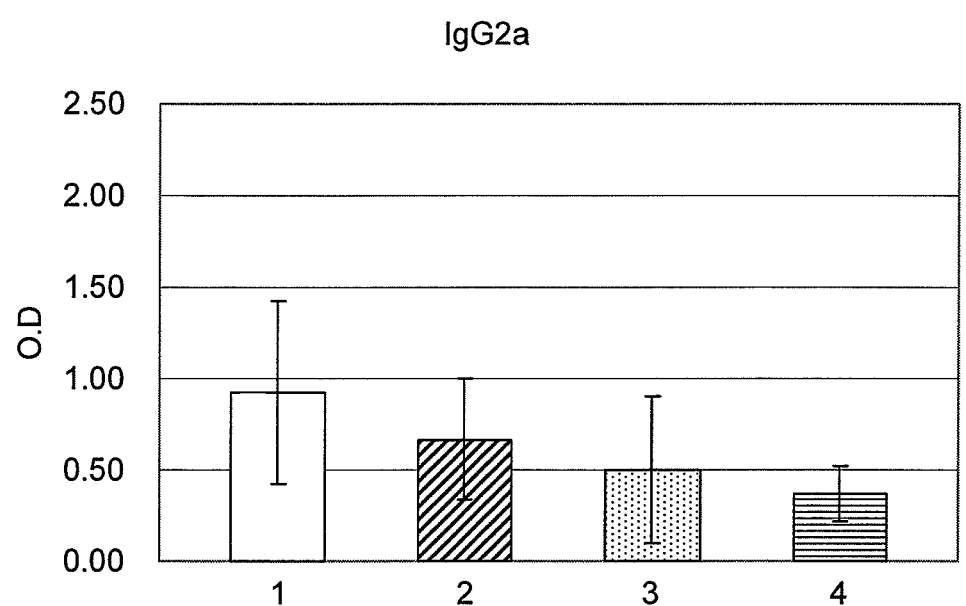
FIG. 1A is a graph showing IgG2a antibody titers in mouse serum when a vaccine composition comprising β-hematin and Alum adjuvant as an adjuvant is administered twice to mice.

The present invention will be described in detail as follows.

Hemozoin can be purified from erythrocytes infected with *Plasmodium falciparum* according to the method as described in, for example, Infect. Immun. 70: 3939-3943, 2002, Proc. Natl. Acad. Sci. U.S.A. 93: 11865-11870, 1996, and Proc. Natl. Acad. Sci. U.S.A. 88: 325-329, 1991, etc. That is, the erythrocytes infected with *Plasmodium falciparum* are dissolved with saponin, sonicated, and washed 7 to 8 times with 2% SDS (sodium dodecyl sulphate). The resulting precipitates are incubated at 37° C. overnight together with proteinase K of 2 mg/mL. The precipitates are washed three times with 2% SDS and incubated together with 6M urea at room temperature for 3 hours. After that, the precipitates are washed with 2% SDS twice, washed with distilled water 3 to 5 times, and suspended in distilled water.

Beta-hematin is a synthetic hemozoin and can be synthesized according to the method as described in, for example, Proc. Natl. Acad. Sci. U.S.A. 93: 11865-11870, 1996, Proc. Natl. Acad. Sci. U.S.A. 88:325-329, 1991 and J. Immunol. 172: 3101-3110, 2004, etc.

The hemozoin or β-hematin prepared as above is treated in 20 mM sodium hydroxide and 2% SDS at room temperature for two hours to depolymerize the hem polymer, and quantified by measuring the absorbance of 400 nm. The quantification can be performed according to the method as described in, for example, Proc. Natl. Acad. Sci. U.S.A. 93:11865-11870, 1996.

The present invention is directed to a vaccine adjuvant composition comprising an effective amount of the above hemozoin or β-hematin to stimulate an immune response. The vaccine adjuvant means a substance that enhances the vaccine effect when used in combination with a vaccine and elevates the production of an antibody to the immunogen used as the vaccine in the living body. The present invention is also directed to said vaccine adjuvant composition, as well as a vaccine composition including an allergen vaccine comprising an effective amount of allergens to stimulate the immune response or an infection vaccine comprising an antigen of pathogens such as bacteria, viruses, rickettsiae, parasites, and the like. The vaccine adjuvant composition according to the present invention can also be used preferably as an adjuvant for mucosal vaccines. The adjuvant for mucosal vaccines can increase an effect of mucosal vaccines to induce mucosal immune system and can induce and enhance the defense system for bacterial or viral infections in the mucosal membrane. As a result of induction of the mucosal immune system, IgA production is induced in the mucosal membrane.

The amount of hemozoin or β-hematin in the vaccine adjuvant composition and vaccine composition is 5 μM to 3 mM, preferably 7.5 μM to 2 mM, more preferably 10 μM to 2 mM, furthermore preferably 10 μM to 1,000 μM, and still furthermore preferably 50 μM to 500 μM.

Freund's complete adjuvants, killed microorganisms (e.g. killed tubercle bacilli, etc.) and other immunostimulators (e.g. Alum adjuvant, etc.) in addition to hemozoin or β-hematin may be added to the vaccine adjuvant composition of the present invention.

The allergen vaccine is a vaccine to block the action of IgE responsible for allergies by the production of IgG antibody against allergens or to increase type 1 helper T cells (Th1 cells) specific to allergens in vivo, thereby to decrease type 2 helper T cells (Th2 cells) which are involved in allergic symptoms, and thus such an allergen vaccine can suppress the allergic symptoms by desensitization. The allergen vaccine comprises an allergen causing various kinds of allergies. The allergen to be used in combination with the vaccine adjuvant composition of the present invention includes, but not limited to, allergens such as food allergens, house dust allergens, pollen allergens (e.g. cedar pollens, etc.), and animal hairs. Specifically, the pollen allergen includes cedar pollen allergens (Cry j1, Cry j2), ragweed allergens (Amba1, Amba2, Amba5, Ambt5, Ambp5), and *Dactylis glomerata* (orchard grass) allergens (Dacg2), etc.; the food allergen includes casein, lactalbumin, lactoglobulin, ovomucoid, ovoalbumin, and conalbumin, etc.; and the house dust allergen includes mite allergens (Derf1, Derf2, Zen1, Derp1, Derp2), etc. Among these, cedar pollen allergens (e.g. Cry j1) and mite allergens (Zen1, Derf1, Derf2) are particularly desirable.

Examples of the vaccines for use in infectious diseases include inactivated complete vaccine, subunit vaccine, toxoid, and the like. These vaccines impart immunity against pathogens such as bacteria, viruses, rickettsiae, parasites, etc. in animals.

Examples of the vaccines for use in infectious diseases for humans include, for example, vaccines for infections with influenza (e.g. type A influenza, type B influenza, etc.), poliovirus, Japanese encephalitis, tubercle bacillus, papillomavirus, *Plasmodium falciparum*, SARS, avian influenza that may infect humans, typhoid, paratyphoid, black death, whooping cough, epidemic typhus, and the like. In the case of animals other than humans, examples of the infection vaccine include, for examples, those against equine influenza virus, equine herpes virus, equine encephalomyelitis virus, foot-and-mouth disease virus, rabies, feline panleukopenia, feline rhinotracheitis, infectious bovine rhinotracheitis, parainfluenza-3, bovine virus diarrhea, bovine adenovirus, porcine parvovirus, canine adenoviruses, canine distemper virus, canine parvovirus, canine parainfluenza, avian influenza, brucellosis, vibriosis, leptospirosis, clostridial infections, salmonellosis, etc. Among them, vaccines for infectious diseases against *Escherichia coli* (bovine mastitis), *Staphylococcus aureus* (bovine mastitis), *Mycoplasma* (porcine pneumonia), PRRS virus (porcine pneumonia), canine rabies virus, etc. are desirable.

Furthermore, the vaccine adjuvant composition comprising hemozoin or β-hematin of the present invention may also be used as an adjuvant for tumor vaccines. It may be used as an adjuvant when a particular tumor specific antigen is administered as a tumor vaccine. It can be used as an adjuvant for any tumor vaccines because the kind of the tumors is not limited.

In the present invention, the vaccine adjuvant composition comprising hemozoin or β-hematin may be used alone. In this case, the vaccine adjuvant composition and the above vaccine may be administered separately to animals. In addition, the vaccine adjuvant composition and the vaccine may be used in the mixed form, and, in this case, a vaccine composition comprising hemozoin or β-hematin can be used.

Animals to which the vaccine adjuvant composition and the vaccine composition of the present invention are to be administered are not particularly limited, but limited only to any animals having an immune system, including mammals, birds, etc. The mammals include human, monkey, cow, horse, pig, sheep, goat, dog, cat, guinea pig, rat, mouse, etc. Birds include chicken, duck, goose, etc. The vaccine adjuvant composition and the vaccine composition according to the present invention are particularly useful as allergy vaccine and infection vaccine for humans, allergy vaccine and infection vaccine for pet animals such as dogs, cats, etc., and infection vaccine for industry animals such as cows, pigs, chickens, etc.

The amount of antigen in the vaccine composition may be varied depending on the kind of infections to be targeted and animal species to be administered, etc., but it is usually in a range of several tens of nanograms to several milligrams per single administration.

The vaccine adjuvant composition and the vaccine composition of the present invention may be in the form of an aqueous or non-aqueous sterilized solution, suspension, or emulsion. Moreover, such composition may comprise a pharmaceutically acceptable diluent, an auxiliary agent, and a carrier, etc., such as salt, buffer, etc. The vaccine compositions can be vaccinated through various routes, such as oral, nasal, transmucosal, intramuscular, subcutaneous, intranasal, intratracheal, cutaneous, percutaneous, or intradermal routes. The vaccine adjuvant compositions and the vaccine compositions of the present invention may be incorporated into drinking water or foods and fed to an animal. The present invention includes drinking water and foods comprising the vaccine adjuvant composition and the vaccine composition of the present invention.

The vaccine adjuvant composition and the vaccine composition of the present invention may be administered even as a single dose or several times at intervals of two days to eight weeks. In this case, the vaccine adjuvant composition or the vaccine composition comprising hemozoin or β-hematin with the above concentration may be administered in 0.1 mL to 2 mL per single administration, preferably 0.5 mL to 1.5 mL per single administration. Further, other immunostimulator such as Alum adjuvant, etc. may be added in 100 μg to 10 mg per single administration, preferably 0.5 mg to 5 mg per single administration.

By administering the vaccine adjuvant composition together with the vaccine of the present invention to an animal, or by administering the vaccine composition of the present invention to an animal, Th1 immunoreaction is induced to increase Th1 cells and to reduce the production of allergy-specific IgE antibody, resulting in elevated production of IgG2 antibody or IgG2a antibody acting as a protective antibody in infectious diseases. As a result, such allergic symptoms can be suppressed in animals, as well as allergic diseases can be treated. In addition, infections can be prevented or treated. Moreover, immune cells such as monocytes and dendritic cells expressing Toll-like receptor 9 (TLR9) are activated by administering the vaccine composition of the present invention to an animal. As a result, infectious diseases can be prevented or treated by cellular immunity. Furthermore, tumors can be prevented or treated by administering the vaccine composition of the present invention to an animal.

EXAMPLES

The present invention is described in detail with reference to the following Examples, whereas the present invention is not limited thereto.

Example 1

Adjuvant Effect of β-Hematin on Mite Allergen Vaccine in Mice

Beta-hematin was prepared by the following method.

Hemin (Fuluka, Netherlands) as raw material (0.45 g) was dissolved in 1M aqueous NaOH solution (Kanto Chemical Co. Inc.) (45 mL), and to this solution was added 0.45 mL of 1M aqueous HCl solution (Kanto Chemical Co. Inc.). The solution was warmed to 60° C., and then acetic acid (Wako Pure Chemical Industries, Ltd.) was dropwise added thereto at 60° C. so as to adjust the pH to 4.8. After allowing to stand overnight at room temperature or for 2 hours at 37° C., the solution was centrifuged (10,000 rpm, 4° C., 10 min), subjected to centrifugal washings four times with a sodium bicarbonate buffer solution (pH 9.1; Wako Pure Chemical Industries, Ltd.)/2% SDS (Wako Pure Chemical Industries, Ltd.), and washed similarly with purified water until the supernatant became transparent light-brown. Afterwards, the product was dispersed in purified water using supersonic waves (PCT-204, manufactured by Sharp Corporation) and then used.

In addition, as for the synthesized β-hematin, a β-hematin sample was dissolved in 0.1M NaOH/SDS solution, and absorbance at 400 nm was measured to calculate the amount of heme as 1.0 of OD (400 nm)=10 nmol/mL) in terms of the OD values, and the solution was used in the subsequent test.

Five-week-old female BALB/c mice were used as animals to be vaccinated.

An allergen Derf2 from *Dermatophagoides farinae* was used as a vaccine. Derf2 was produced as a recombinant Derf2 in a silkworm-baculovirus gene expression system by the following method. cDNA of the allergen Derf2 from *Dermatophagoides farinae* was amplified by PCR, and linked to a plasmid vector pBM030, and the obtained recombinant plasmid was transformed to *E. coli* TOP10 strain (manufactured by Invitrogen). After the transformant strain had been cultured in LB medium containing 100 μg/ml of ampicillin at 37° C. for 8 hours, the recombinant plasmid DNA was purified with a QIAGEN Midi kit (manufactured by QIAGEN). The produced and purified recombinant pBM030 plasmid DNA 2 μg and baculovirus DNA (1 cut BmNPV DNA, manufactured by Nosan Corporation) 20 ng were mixed, and a recombinant baculovirus wherein Derf2 cDNA had been integrated into the genome was created and isolated by the usual method. Then, the recombinant baculovirus strain adjusted to 5×10⁴ to 5×10⁷ PFU/ml was inoculated to the fifth instar larva of silkworm, thereby to express a recombinant Derf2 in the body fluid of the silkworm. The collected body fluid of the silkworm was diluted 10-fold with 50 mM acetic acid buffer solution of pH 4.0, and centrifuged at 4° C. and 3,000 rpm for 10 minutes to collect the supernatant fraction. The supernatant fraction was purified using a cation exchange column (TOYOPEARL SP-550C, manufactured by TOSOH Corporation) and an anion exchange column (Q Sepharose Fast Flow, manufactured by GE Healthcare Corporation), and quantified by ELISA method for use in the following examination.

Beta-hematin as an adjuvant was added to 1 μg or 2 μg of the recombinant Derf2 to become a concentration of 1 mM in 300 μl and then mixed with 100 μg of Alum adjuvant. After adjustment to 300 μl with PBS, the solution was intraperitoneally inoculated to the above four mice each. In this case, a mixture of the recombinant Derf2 and Alum adjuvant without mixing with the β-hematin was inoculated as a control. The vaccination was performed three times every one week.

Grouping of all 15 mice is as follows.
a Derf2 2 μg+β-hematin 1 mM+Alum adjuvant 100 μg
b Derf2 1 μg+β-hematin 1 mM+Alum adjuvant 100 μg
c Derf2 2 μg+Alum adjuvant 100 μg
d Derf2 1 μg+Alum adjuvant 100 μg Blood sample was collected from the mice one week after the second and third vaccinations to separate the serum, and Derf2-specific IgG1 and IgG2a were measured by ELISA.

Figure 1B:
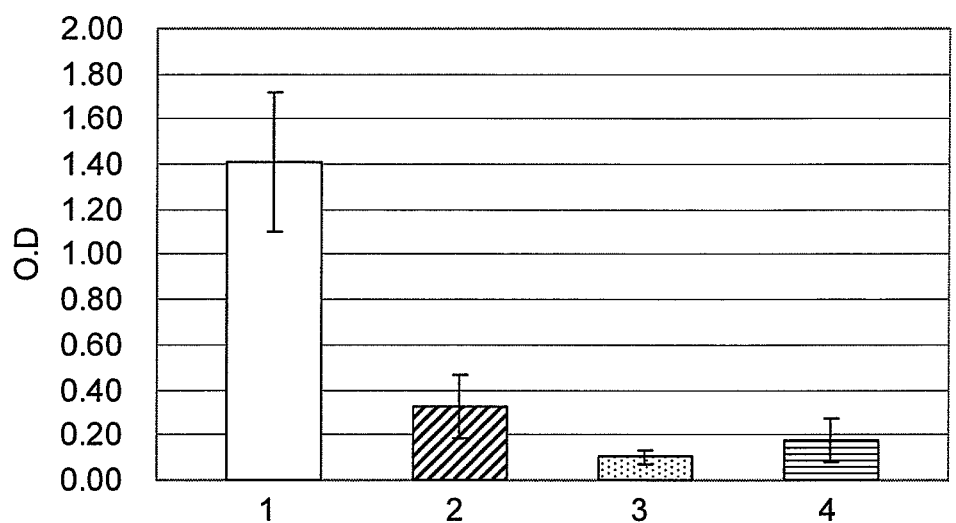
FIG. 1B is a graph showing IgG1 antibody titers in mouse serum when a vaccine composition comprising β-hematin and Alum adjuvant as an adjuvant is administered twice to mice.
Figure 2A:
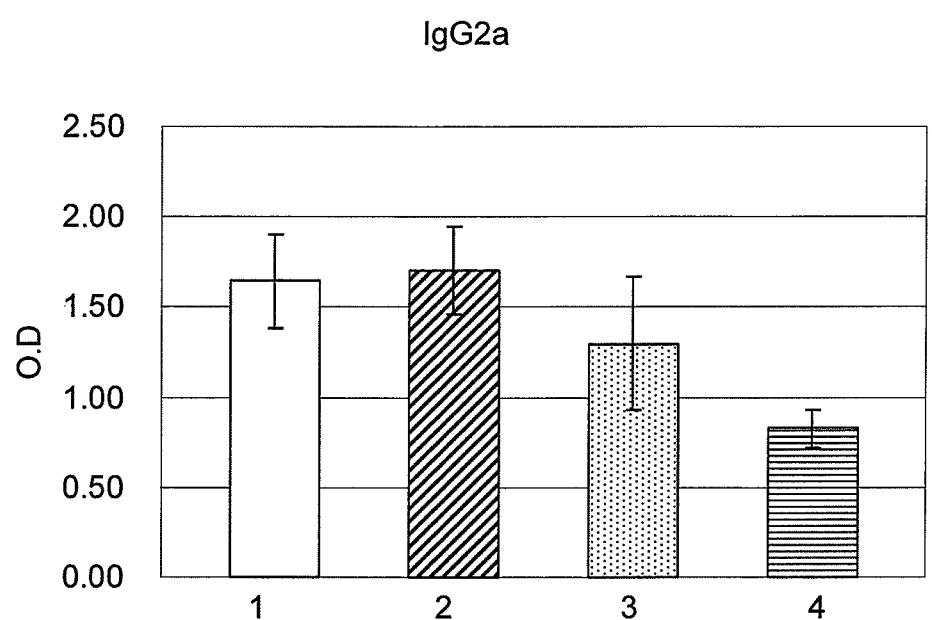
FIG. 2A is a graph showing IgG2a antibody titers in mouse serum when a vaccine composition comprising β-hematin and Alum adjuvant as an adjuvant is administered three times to mice.
Figure 2B:
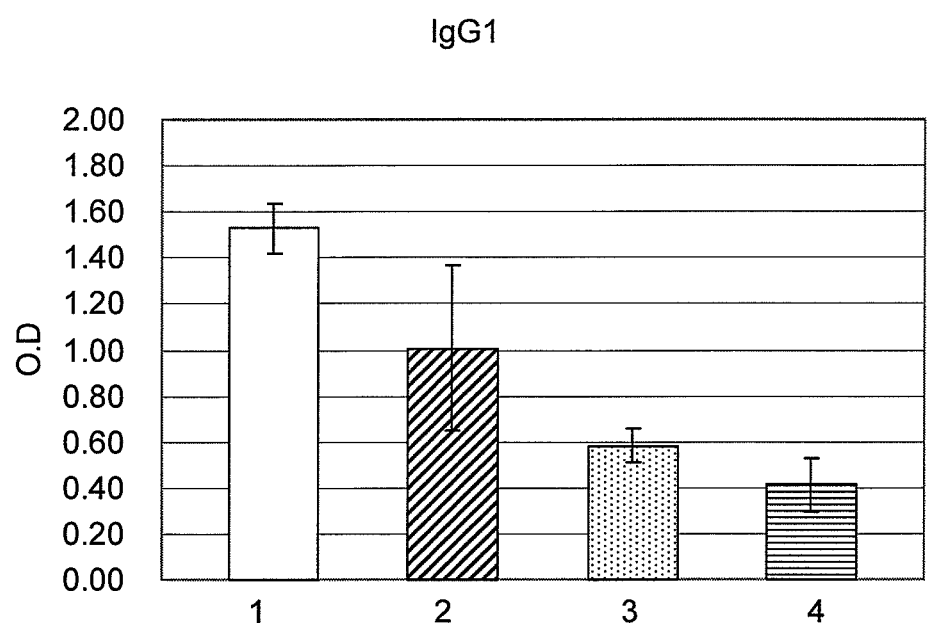
FIG. 2B is a graph showing IgG1 antibody titers in mouse serum when a vaccine composition comprising β-hematin and Alum adjuvant as an adjuvant is administered three times to mice.

FIGS. 1A and 1B show antibody titers in the serum from the blood collected one week after the second inoculation. FIG. 1A is a measurement result of IgG2a, and FIG. 2B is a measurement result of IgG1. Further, FIGS. 2A and 2B show antibody titers in the serum from the blood collected one week after the third inoculation. FIG. 2A is a measurement result of IgG2a, and FIG. 2B is a measurement result of IgG1.

As shown in Figures, both IgG2a antibody titer and IgG1 antibody titer were more elevated when β-hematin was added, as compared with the case where β-hematin was not added.

Example 2

Adjuvant Effect of β-hematin on Mite Allergen Vaccine in Dogs

Approximately five-month-old beagle dogs were used as animals to be vaccinated.

An allergen Derf2 from *Dermatophagoides farinae* was used as a vaccine. Recombinant Derf2 was produced by using silkworms, and β-hematin as adjuvant was mixed with 100 μg of the recombinant Derf2 to become a concentration of 7.5 or 15 μM in 1 mL of the vaccination dose. In addition, six kinds of vaccines in all were prepared with or without addition of Alum adjuvant. One mL of each vaccine was subcutaneously inoculated to the above four beagle dogs, respectively. In this case, recombinant Derf2 which had been mixed with only Alum adjuvant, and recombinant Derf2 only which had not been mixed with β-hematin and Alum adjuvant as a control were inoculated. The vaccination was performed twice at intervals of two weeks.

Grouping of all 24 beagle dogs is as follows.
a Derf2 100 μg+O-hematin 15 μM+Alum adjuvant 0.5 mg
b Derf2 100 μg+β-hematin 7.5 μM+Alum adjuvant 0.5 mg
c Derf2 100 μg+Alum adjuvant 0.5 mg
d Derf2 100 μg+β-hematin 15 μM
e Derf2 100 μg+β-hematin 7.5 μM
f Derf2 100 μg Blood was collected from the beagle dogs before the vaccination and on day 7, 14, 21 and 28 after the first vaccination, and the serum was separated, and Derf2-specific IgG1 and IgG2 were measured by ELISA.

Figure 3A:
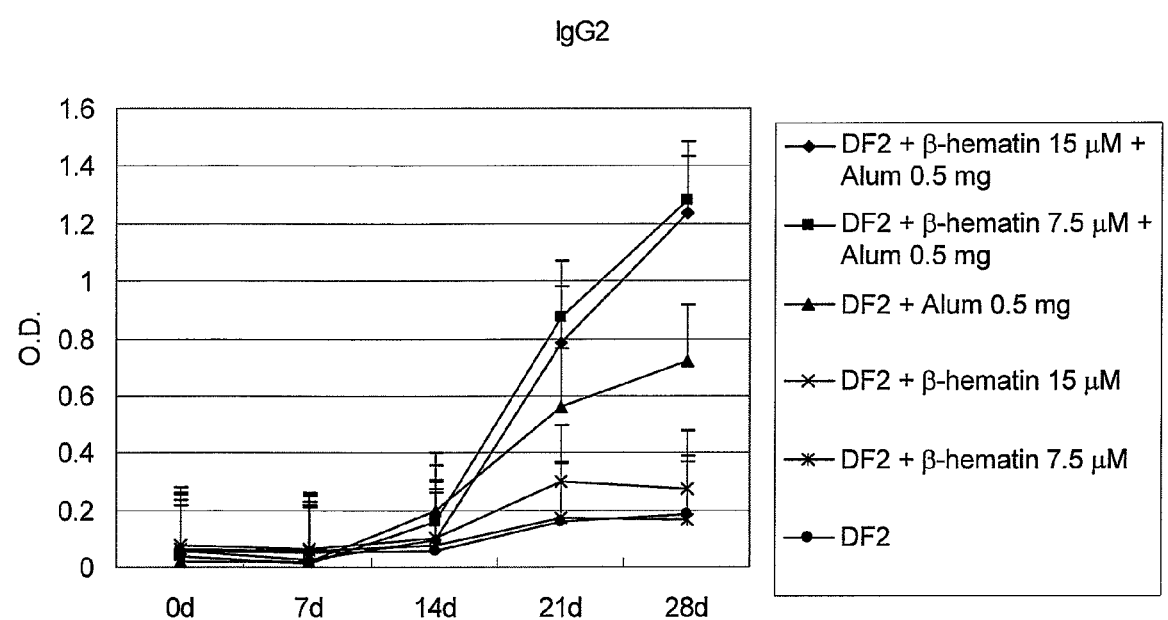
FIG. 3A is a graph showing change in IgG2 antibody titers in canine serum with time when a vaccine composition comprising β-hematin as an adjuvant is administered to dogs.
Figure 3B:
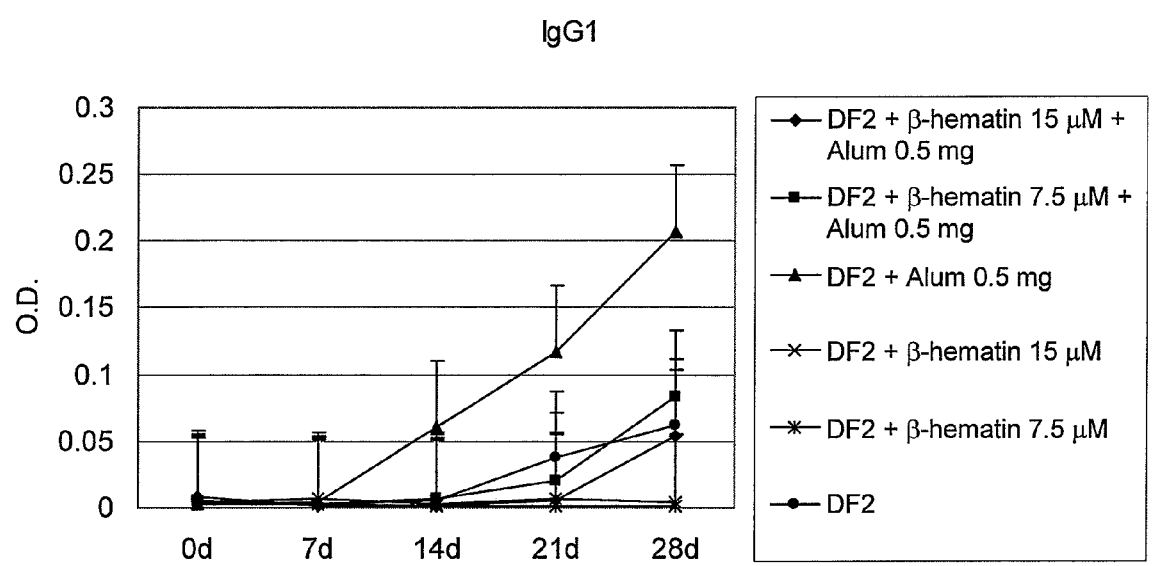
FIG. 3B is a graph showing change in IgG1 antibody titers in canine serum with time when a vaccine composition comprising β-hematin as an adjuvant is administered to dogs.
Figure 4A:
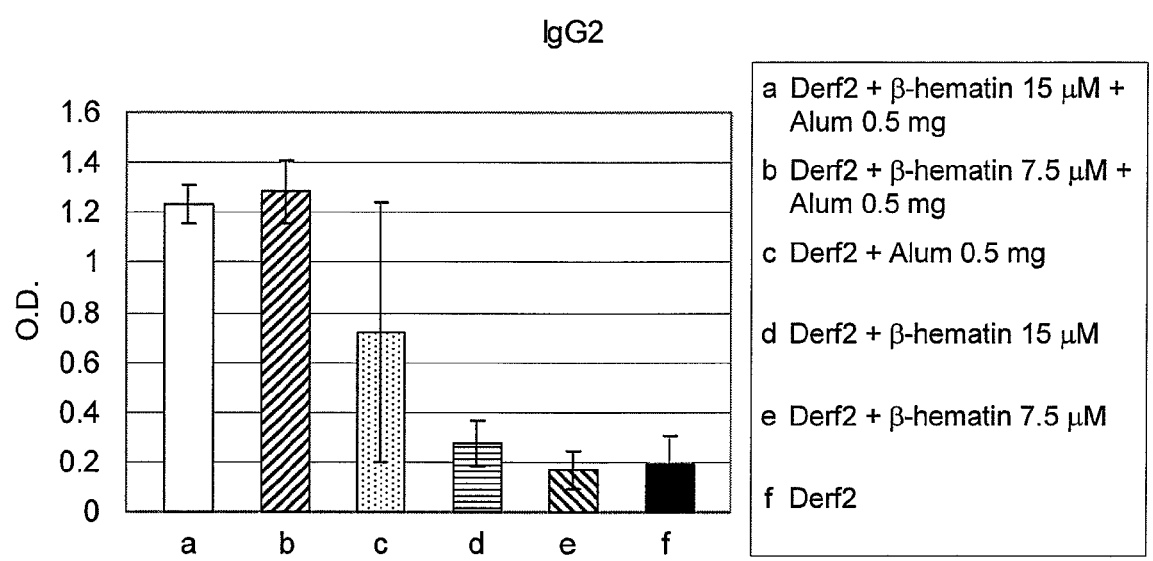
FIG. 4A is a graph showing IgG2 antibody titers in canine serum when a vaccine composition comprising β-hematin as an adjuvant is administered to dogs.
Figure 4B:
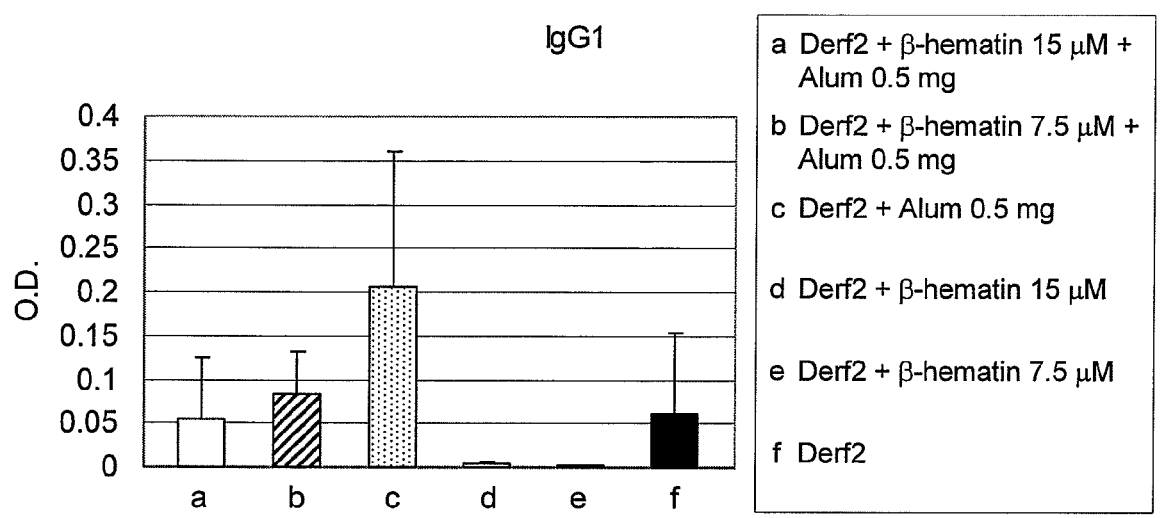
FIG. 4B is a graph showing IgG1 antibody titers in canine serum when a vaccine composition comprising β-hematin as an adjuvant is administered to dogs.

FIG. 3 shows the change with time of antibody amount of each group. FIG. 3A shows the result of the measurement of IgG2, and FIG. 3B shows the result of the measurement of IgG1. FIG. 4 shows the antibody amount of each group in the serum collected on day 28 (on day 14 after the second vaccination) after the first vaccination. FIG. 4A shows the result of the measurement of IgG2, and FIG. 4B shows the result of the measurement of IgG1. As shown in Figures, when β-hematin was inoculated together with IgG2 and IgG1, the antibody titer is more elevated with time, compared to the case where no adjuvant was used. Further, when IgG2 was used in combination with β-hematin and Alum adjuvant, the maximum antibody titer rise was observed.

Example 3

Adjuvant Effect of β-Hematin on Mite Allergen Vaccine in Dogs (Part 2)

Approximately five-month-old beagle dogs were used as animals to be vaccinated.

An allergen Derf2 from *Dermatophagoides farinae* was used as a vaccine. Recombinant Derf2 was produced by using silkworms, and β-hematin as adjuvant was mixed with 100 µg of the recombinant Derf2 to become a concentration of 1 mM or 2 mM in 1 mL of the vaccination dose. Further, one mg of Alum adjuvant was mixed with the vaccine to prepare two kinds of vaccines. 1 mL of each vaccine was subcutaneously inoculated to the above four beagle dogs, respectively. In this case, recombinant Derf2 which had been mixed with only Alum adjuvant was inoculated as a control. The vaccination was performed twice at intervals of two weeks.

Grouping of all 12 beagle dogs is as follows.
a Derf2 100 µg+β-hematin 2 mM+Alum adjuvant 1 mg
b Derf2 100 µg+β-hematin 1 mM+Alum adjuvant 1 mg
c Derf2 100 µg+Alum adjuvant 1 mg Blood was collected from the beagle dogs before the vaccination and three weeks and four weeks after the first vaccination, and then the serum was separated, and Derf2-specific IgG2 was measured by ELISA.

The results are shown in FIG. 5. In FIG. 5, 1-6 show the following results.

1. Derf2 100 µg+β-hematin 2 mM+Alum adjuvant 1 mg (Blood sample was taken 3 weeks after the administration)
2. Derf2 100 µg+β-hematin 1 mM+Alum adjuvant 1 mg (Blood sample was taken 3 weeks after the administration)
3. Derf2 100 µg+Alum adjuvant 1 mg (Blood sample was taken 3 weeks after the administration)
4. Derf2 100 µg+β-hematin 2 mM+Alum adjuvant 1 mg (Blood sample was taken 4 weeks after the administration)
5. Derf2 100 µg+β-hematin 1 mM+Alum adjuvant 1 mg (Blood sample was taken 4 weeks after the administration)
6. Derf2 100 µg+Alum adjuvant 1 mg (Blood sample was taken 4 weeks after the administration)

As shown in FIG. 5, IgG2 antibody titer was remarkably elevated when β-hematin was added. Further, in the serum from the blood collected 4 weeks after the administration, more dose of β-hematin raised the IgG2 antibody titer. The IgG1 antibody titer rise was not recognized in any individual dogs.

Example 4

Adjuvant Effect of Beta-Hematin on Bacterial Infections

Antibody inducibility was evaluated in mice when β-hematin was used as an adjuvant for cow mastitis vaccine.
1. Bacterial Strain Used as Vaccine Antigen
*Escherichia coli* J5 strain was used as a vaccine antigen.
2. Preparation of Inactivated *Escherichia coli* Antigen
A bacterial stock solution was added to 1 L of Tryptic Soy Broth (manufactured by BD Difco), and shaking-cultured at 37° C. for 6 hours. After centrifugation (10,000 rpm, 10 min) of the culture, the cells were suspended in 0.4% formalin-added PBS (100 mL), and stirred at 25° C. for one day to inactivate them. The inactivated bacterial solution was centrifuged and the resulting cells were resuspended in 100 mL of PBS, and then centrifuged in the same way. After repeating this washing process of the cells three times in total, the resulting cells were suspended in 50 mL of PBS and the suspension was served as an undiluted antigen solution. As for the bacterial solution after the cultivation, it was diluted by a 10-fold serial dilution method and each diluted solution was streaked on Tryptic Soy Agar (manufactured by BD Difco) to count the number of the bacteria.

3. Setting of Test Groups and Number of Test Animals

Thirty-five mice were divided into the following test groups (5 groups; seven mice each).

Administration group (seven mice) of β-hematin 100 µM
Administration group (seven mice) of β-hematin 40 µM
Administration group (seven mice) of β-hematin 20 µM
Non-administration group (seven mice) of β-hematin
Non-vaccination group (seven mice)

4. Test Animals

Thirty-five mice (ddy, female) of five weeks of age were used.

5. Preparation of Vaccine

Hematin was adjusted to have a concentration of 100, 40 or 20 µM in 0.5 mL of the vaccination dose when added to the inactivated bacterial solution which had been adjusted to $10^9$ CFU/mL with PBS, and then 40 µg of aluminum hydroxide gel (Alum) was added thereto, whereby to prepare a β-hematin-added vaccine. Only aluminum hydroxide gel (40 µg) was added to the inactivated bacterial solution which had been adjusted to $10^9$ CFU/mL with PBS, thereby to prepare a vaccine without addition of β-hematin.

6. Mouse Test

After introduction of mice, they were subjected to preliminary breeding for one week, and received subcutaneously 0.5 mL each of the prepared vaccine at intervals of two weeks. Blood sample was taken from a tail vein every one week after the introduction, while whole blood was collected two weeks after the second vaccination, and antibody titer was measured by ELIZA using the resulting serum.

Figure 6:
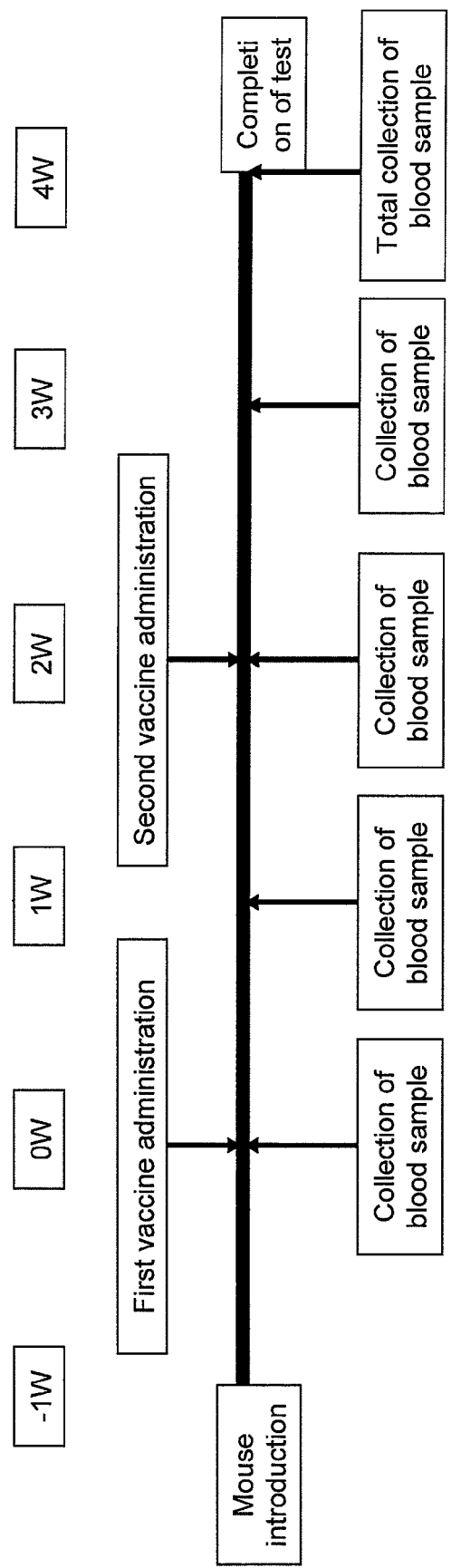
FIG. 6 is a diagram showing the test schedule to confirm the adjuvant effect on bacterial infections by a vaccine composition comprising β-hematin and Alum adjuvant as an adjuvant.

Test schedule is shown in FIG. 6.

7. Measurement of Antibody Titer by ELISA

Antiserum of *Escherichia coli* J5 strain was immobilized on an immunoplate, and after blocking with 0.1% gelatin-added PBS (diluted solution), the inactivated antigen solution of *E. coli* J5 strain was served as an antigen-adsorbed plate. Test serum was diluted 100-fold with the diluted solution and the resulting diluted solution was served as a stock solution, which was then further diluted by the 2-fold serial dilution method. The diluted serum (0.05 mL) was added to the antigen-adsorbed plate and reacted overnight at 4° C. After washing the plate five times with 0.05% Tween 20™-added PBS (washing solution), 0.1 mL each of labeled antibody (prepared by diluting peroxidase-labeled anti-mouse IgG1 and IgG2 antibodies with a blocking solution) was added to each well, and reacted at 37° C. for one hour. After five times washing with the washing solution, a substrate solution (diammonium 2,2'-azino-bis(3-ethylbenzothiazoline-6-sulfonate 45 mg) was dissolved in 1 mL of water, and a portion 0.15 mL of this solution and 0.05 mL of 5% hydrogen peroxide solution were added to 10 mL of a substrate buffer solution [prepared by mixing Solution A (prepared by dissolving 21.0 g of citric acid monohydrate in water to make the total volume to 1,000 mL) with Solution B (prepared by dissolving 29.4 g of trisodium citrate dihydrate in water to make the total volume to 1,000 mL) and adjusting the pH to 4.0], and 0.1 ml each of the resulting mixture was added to each well, and the reaction was performed at 37° C. for 20 minutes. Then, 0.32% sodium fluoride solution was added to each well in 0.05 mL each to stop the reaction, and the absorbance at a wavelength of 415 nm was measured. Two-fold values of the mean absorbance values of the control serum were regarded as the cutoff value, and the antibody titers were expressed as a reciprocal of the highest dilution multiple of the serum indicating the absorbance value not less than the cut off value.

Figure 7:
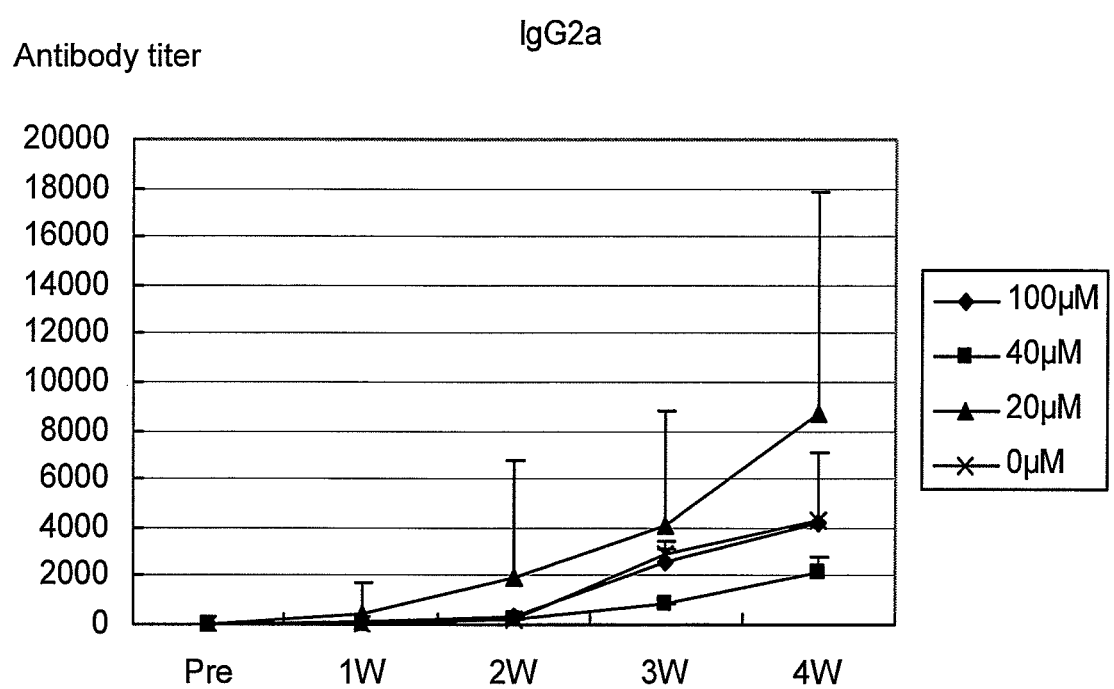
FIG. 7 is a graph showing antibody titers of a bacteria-specific IgG2a antibody induced by a vaccine composition comprising β-hematin as an adjuvant.
Figure 8:
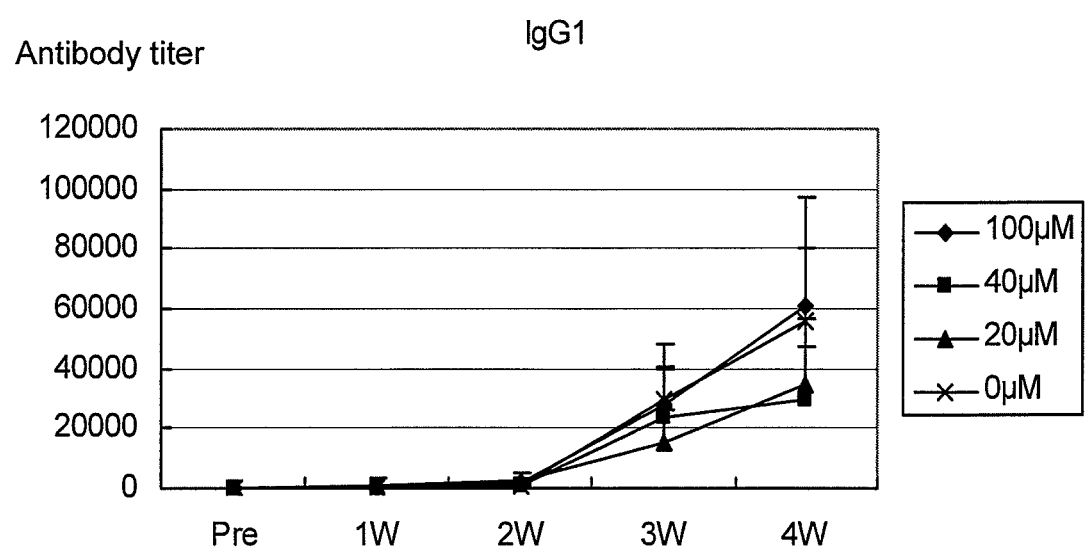
FIG. 8 is a graph showing antibody titers of a bacteria-specific IgG1 antibody induced by a vaccine composition comprising β-hematin as an adjuvant.
Figure 9:
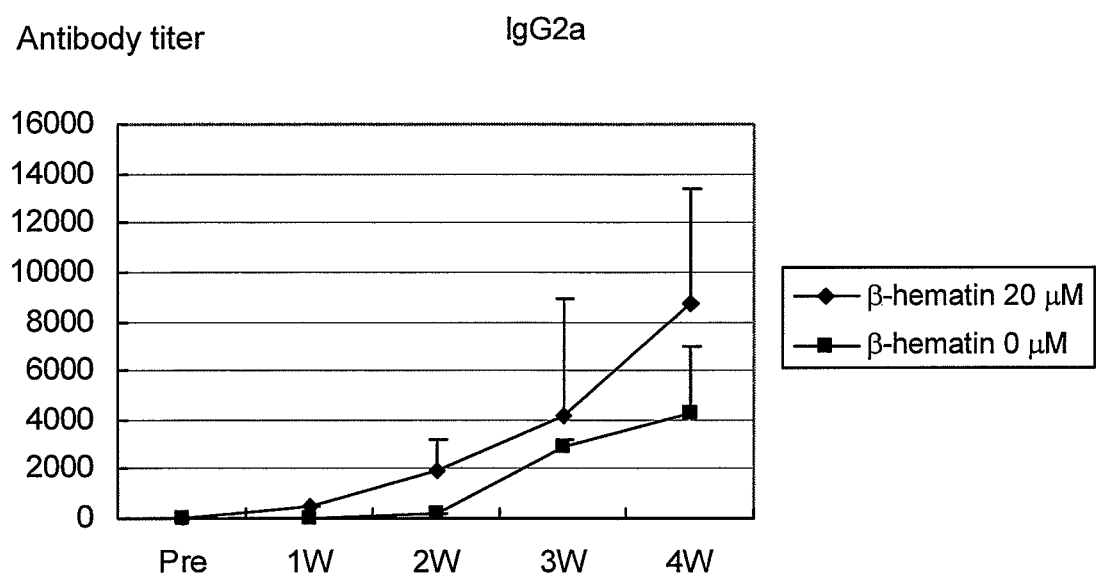
FIG. 9 is a graph showing antibody titers of a bacteria-specific IgG2a antibody induced by a vaccine composition comprising β-hematin as an adjuvant (part 2).
Figure 10:
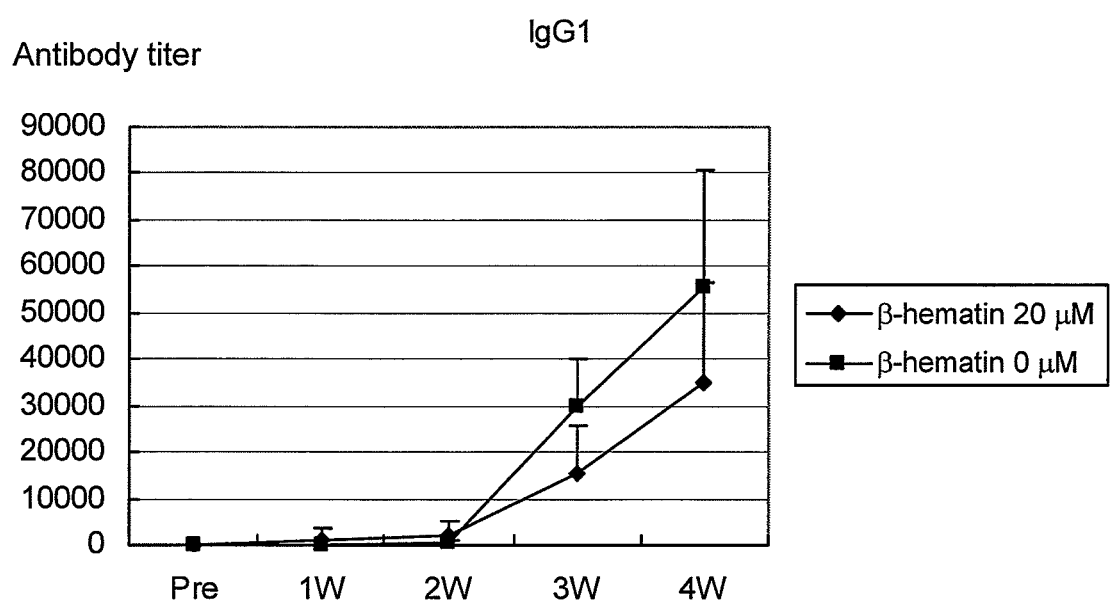
FIG. 10 is a graph showing antibody titers of a bacteria-specific IgG1 antibody induced by a vaccine composition comprising β-hematin as an adjuvant (part 2).

FIG. 7 shows E. coli-specific IgG2a antibody titers with time of mice receiving 20, 40, and 100 μM of β-hematin and mice not receiving β-hematin, and FIG. 8 shows E. coli-specific IgG1 antibody titers with time. Further, FIG. 9 shows E. coli-specific IgG2a antibody titers with and without administration of 20 μM of β-hematin, and FIG. 10 shows E. coli-specific IgG1 antibody titers with time.

As shown in Figures, it became clear that Th1 induction by the addition of β-hematin was not concentration-dependent and was the highest when 20 μM of β-hematin was added.

Example 5

Adjuvant Effect of β-Hematin on Virus Infections

Using a wild strain (inactivated) of porcine reproductive and respiratory syndrome virus/PRRSV, adjuvant effect of β-hematin on infections was studied in mice.
Selection of Strains PRRSV JFS04-07, 05-01, 05-02, and 05-03 strains which had been isolated and stocked by Nippon Zenyaku Kogyo Co., Ltd. were respectively inoculated to MARC145 cells (PRRSV-sensitive kidney cells from Macaca mulatta (rhesus macaque or rhesus monkey)), and observation was made on the occurrence of CPE. After approximately one week, PRRSV JFS04-07 strain showing CPE was used in this Example. When PCR method to detect the PRRSV gene was performed for each strain, gene amplification was not recognized in the three strains except for the PRRSV JFS04-07 strain.
Preparation of Immunogen The PRRSV JFS04-07 strain was inoculated to MARC145 cells seeded into sixteen 175T flasks, frozen and thawed three times after confirmation of CPE, and centrifuged at 5,000 rpm for 30 minutes to collect a culture supernatant of approximately 800 mL. The culture supernatant was centrifuged at 35,000 rpm for 4 hours using 30% sucrose as a cushion. After centrifuge, the resulting pellet was suspended in 6 mL of PBS.

As a result of having performed titration and protein quantification (with use of a Coomassie Protein Assay Reagent Kit) about the suspension, the infection titer was found to be $10^{6.30}$ TCID$_{50}$/mL and the protein amount was found to be about 1,000 μg/mL.

Beta-propiolactone was added to the suspension to have a final concentration of 0.1%, stirred, and reacted overnight at 37° C. for inactivation. This was used as an immuogen.
Mouse Test Total four groups of β-hematin (10 μM) addition group, β-hematin (5 μM) addition group, β-hematin no addition group and a control group were set as follows. One mouse was used as the control group, and seven mice each were used in other groups. Beta-hematin was prepared to make 10 μM or 5 μM in 200 μL of the inoculum dose, and aluminium hydroxide gel (Alum) 80 μg was added thereto.

(i) Inactivated PRRSV+β-hematin (10 μM)+Alum administration group (β-hematin addition group)
(ii) Inactivated PRRSV+β-hematin (5 μM)+Alum administration group β-hematin addition group)
(iii) Inactivated PRRSV+Alum administration group (β-hematin no addition group)
(iv) Control group (no administration)

Five-week-old BALB/c (female) mice (introduced at 4 weeks of age and acclimated for one week) were used in this test.

For immunization, mice received intraperitoneally 200 μL each of the vaccines per one mouse twice at intervals of two weeks. Two weeks later from the second immunization, whole blood was drawn from the heart, and serum was collected. The collected serum was placed in an Eppendorf tube and kept at −20° C.
Preparation of Antigen for ELISA The PRRSV JFS04-07 strain was inoculated to MARC145 cells seeded into twenty-four 175T flasks, frozen and thawed three times after confirmation of CPE, and centrifuged at 5,000 rpm for 30 minutes to collect a culture supernatant of approximately 1,200 mL. The culture supernatant was centrifuged at 35,000 rpm for 4 hours using 30% sucrose as a cushion. After centrifuge, the resulting pellet was suspended in 7 mL of PBS.

As a result of having performed titration and protein quantification (with use of a Coomassie Protein Assay Reagent Kit) about the suspension, the infection titer was found to be $10^{5.80}$ TCID$_{50}$/mL and the protein amount was found to be about 1,200 μg/mL.

Beta-propiolactone was added to the suspension to have a final concentration of 0.1%, and the mixture was stirred and reacted overnight at 37° C. for inactivation. This was used as an immuogen for ELISA.
Measurement of Antibody Titer (ELISA)

An ELISA system by box titration was constructed using the collected mouse serum and the prepared antigen for ELISA. As a result, 1.2 μg/mL of the antigen for ELISA was used in the immobilization. The mouse serum was diluted 8,000-fold to 2-fold by the serial dilution method, and HRP-labeled anti-mouse total IgG antibody, anti-mouse IgG1 antibody and anti-mouse IgG2a antibody were used as the second antibody. After the reaction of the second antibody, color development with TMB reagent was performed, and OD values at 450 nm/570 nm were measured after stopping the color reaction.

HRP-labeled anti-mouse total IgG, anti-mouse IgG1 and anti-mouse IgG2a were reacted as the second antibody, and each IgG subclass was detected. From the obtained OD values, (mean of OD values of control group)×2 was regarded as the cut off value, and the value not less than the cut off value was expressed as an antibody tier.

The results were as follows.

Figure 11:
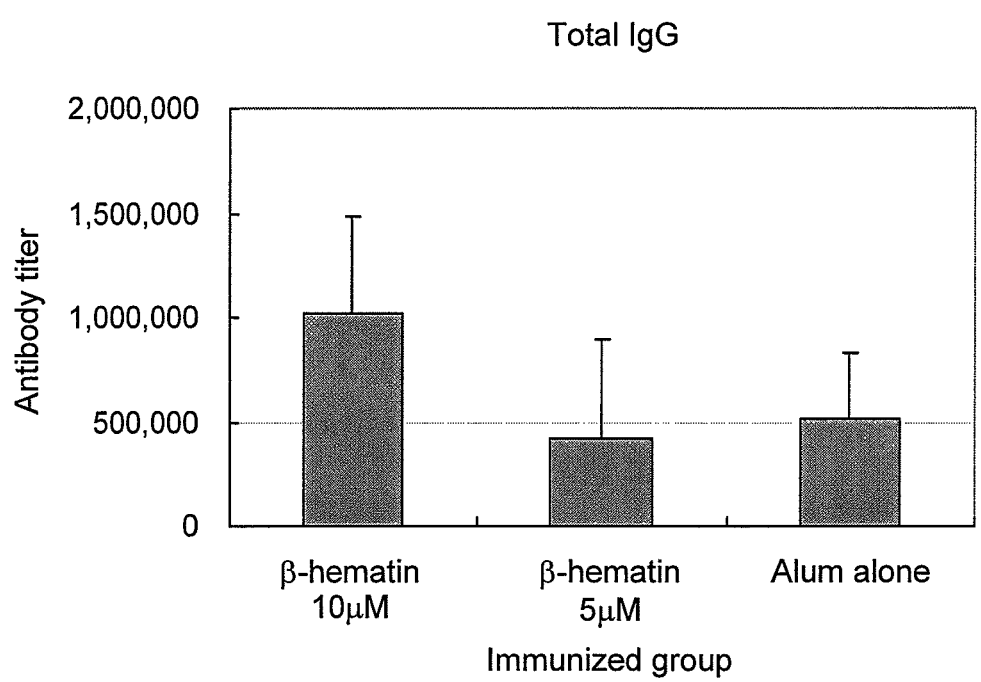
FIG. 11 is a graph showing antibody titers of a virus-specific total IgG antibody induced by a vaccine composition comprising β-hematin as an adjuvant.

As for the total IgG, the β-hematin 10 μM addition group showed a higher antibody titer in geometric mean value than the β-hematin no addition group by 512,000 (FIG. 11).

Figure 12:
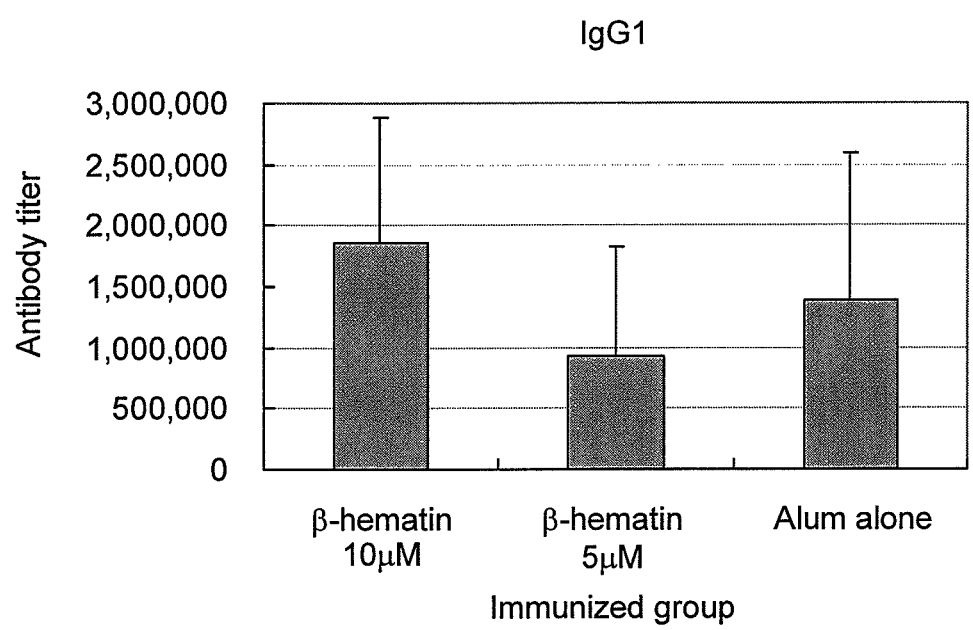
FIG. 12 is a graph showing antibody titers of a virus-specific IgG1 antibody induced by a vaccine composition comprising β-hematin as an adjuvant.

As for the IgG1, the β-hematin 10 μM addition group showed a higher antibody titer in geometric mean value than the β-hematin no addition group by 470,000 (FIG. 12).

Figure 13:
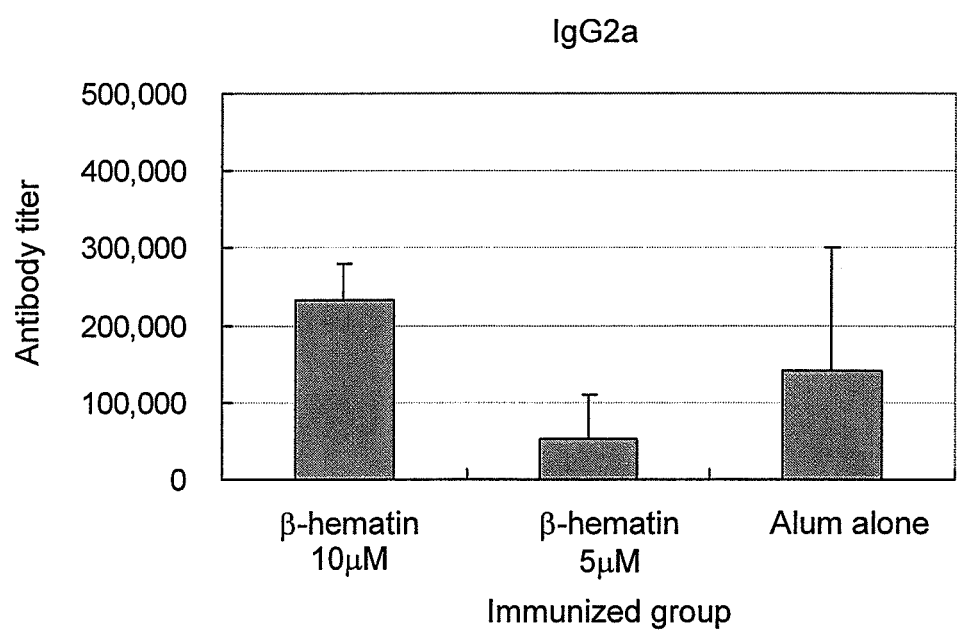
FIG. 13 is a graph showing antibody titers of a virus-specific IgG2a antibody induced by a vaccine composition comprising β-hematin as an adjuvant.

As for the IgG2a, the β-hematin 10 μM addition group showed a higher antibody titer in geometric mean value than the β-hematin no addition group by 90,000 (FIG. 13).

From these results in this experiment, it was suggested that a more elevated level of the antibody was recognized in the β-hematin 10 μM addition group than in the β-hematin no addition group.

Especially, what should be paid attention is an IgG2a antibody titer rise. Because it is known that the β-hematin acts on the Th1 type immune system via TLR9 like CpG motif, it is thought from these results that β-hematin acted effectively in the mouse body.

Example 6

Evaluation of β-Hematin on Immunological Action

Figure 14:
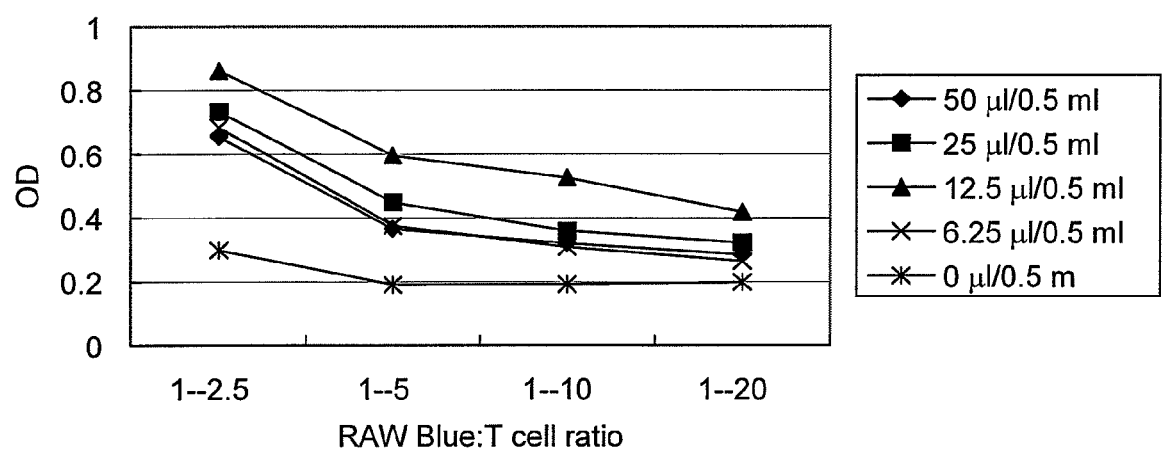
FIG. 14 is a graph showing activation action of monocytes by various doses of β-hematin.
Figure 15:
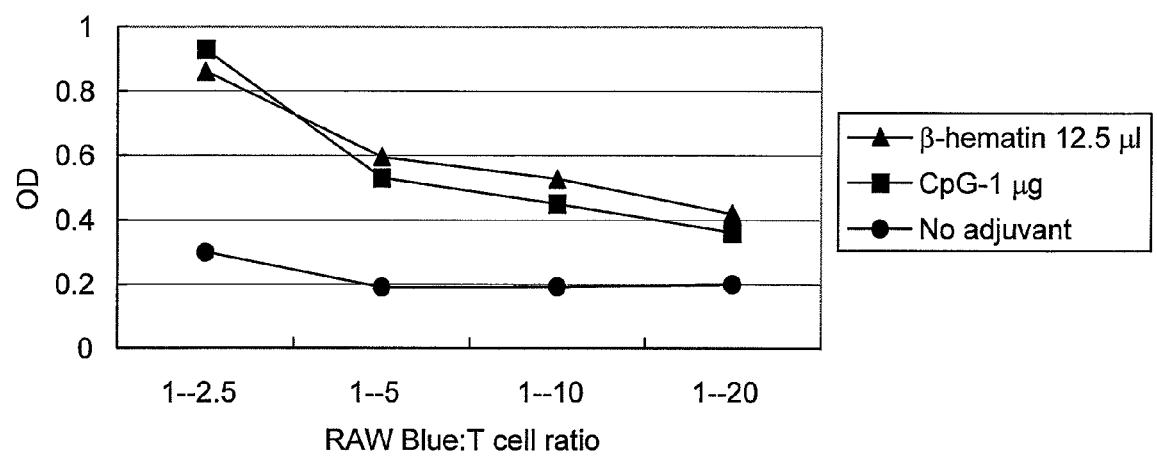
FIG. 15 is a graph showing a comparison between β-hematin and CpG on activation action of monocytes.

Examination on Activation Action of β-Hematin for Dendritic Cells by Mixed Lymphocyte Reaction T-cells derived from allogenic mouse C3H recognize, as a non-self antigen, a MHC molecule expressed on activated RAW-Blue cells (derived from monocyte cell line Balb/c) and show a proliferative activity. Thus, an activation ability to the RAW-Blue cells by β-hematin was evaluated by culturing the RAW-Blue cells under each condition, mixed-culturing them with (C3H)-derived T-cells, and measuring the proliferative activity of T-cells.
Method
i) RAW-Blue cells were seeded to a 24 well plate in $5 \times 10^5$ cells/well (0.5 mL/well), and stimulated and cultured for 48 hours under each condition as shown below.
Culture Conditions
Beta-hematin addition group; 0, 6.25, 12.5, 25, 50 μL (/well)
CpG addition group; 0, 6.25, 12.5, 25, 50 μg/mL (/well)
Non-Addition Group
ii) After stimulation culture, RAW-Blue cells were collected and treated with mitomycin C.
iii) Splenic cells were collected from C3H mice, and T cells were separated using a nylon fiber column.
iv) RAW-Blue cells which had been cultured under each condition were prepared to have a respective constant cell ratio to T cells of $1 \times 10^5$ cells.
v) Mixed culture was performed in a 96-well plate.
vi) Five days later, proliferative activity of T cells was measured using CellTiter96™.
Results FIG. 14 shows T-cell proliferation to the dose of β-hematin. In addition, FIG. 15 shows the effect of β-hematin and CpG on T cell proliferation. The results as shown in FIGS. 14 and 15 suggest that RAW-Blue cells which are a cell strain of monocytes were activated by β-hematin through the mixed lymphocyte reaction.

Example 7

Evaluation of Effect of β-Hematin as Antitumor Vaccine Adjuvant

Beta-hematin was inoculated to biliary-cancer mice model produced by inoculating sarcoma 180 (S180) subcutaneously into ICR mice. After completion of the immunization, cytotoxicity of splenic cells against S180 (antigen) and antigen-specific proliferative activity of splenic cells were measured.
Method
The vaccines of each group below (3 animals/group) were intraperitoneally administered once a week (total three times).
  Group 1: no vaccine administration (control)
  Group 2: S180 lysate+Alum (β-hematin-)
  Group 3: S180 lysate+β-hematin (0.5 mL of 0.1 mM)+Alum (β-hematin+)
In this case, Alum was used at a concentration of 40 mg/mL.

Freezing and thawing of the S180 lysate were repeated three times, and a sonicated sample was prepared to become $10^6$ cells in 10 μL of vaccination dose.

After completion of the immunization, proliferative activity was measured on day 3 after the cultivation and cytotoxicity against S180 was measured on day 5 after the cultivation.

Measurement of Proliferative Activity: The collected mouse splenic cells were cultured in a 96-well plate in the presence of S180. After the cultivation for 3 days, a proliferative activity of the cells was measured by the absorbance using a CellTiter96™.

Figure 16:
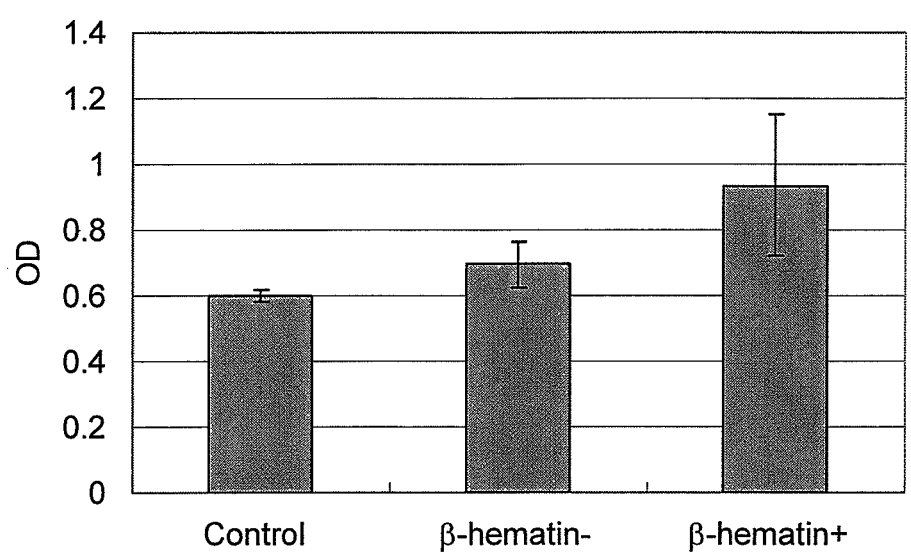
FIG. 16 is a graph showing an effect of β-hematin as an antitumor vaccine adjuvant.

Measurement of Cytotoxicity: The collected mouse splenic cells were cultured in a 96-well plate in the presence of S180. After the cells being restimulated with S180 antigen, the absorbance was measured using Cytotox.
Results The reduction effect on S180 which was subcutaneously inoculated as well as the significantly elevated level of cytotoxicity was not observed in any vaccine groups, but a tendency to show a high proliferative activity against the antigen was recognized in lymphocytes (splenic cells) of the β-hematin-containing vaccine administration group (FIG. 16).

Example 8

Evaluation of Effect of β-Hematin as Mucosa Adjuvant

Confirmation of Effect of β-Hematin as Mucosa Adjuvant Using Mice (Measurement of IgG1 and IgG2a in Serum and IgA in Bronchial and Intestinal Washings)
Method

*Staphylococcus aureus* No. 39 strain that the company had isolated was inactivated with formalin, and the whole cells were served as the antigen, followed by administration into 5-week-old female balb/c mice. The antigen dose was $1 \times 10^9$ CFU. The vaccine dose was 10 μL. The β-hematin was used in doses adjusted to 20 μM, 100 μM and 500 μM, relative to the vaccine dose 10 μL.

Mice were divided into the following administration groups (3 mice/group) of (a)-(d).
  (a) Antigen (SA)+Alum
  (b) SA+Alum+β-hematin (20 μM)
  (c) SA+Alum+β-hematin (100 μM)
  (d) SA+Alum+β-hematin (500 μM)
In this case, Alum was used at a concentration of 40 mg/mL.

The immunization was performed three times by the nasal administration. The serum and the bronchial and intestinal washings were collected as a sample one week after the third immunization. The SA-specific IgG1 and IgG2 in the serum and IgA (BALF IgA) in the bronchial and intestinal washings were measured by ELISA.

The bronchial washing fluid was collected by the following method.
1. An injection needle with an outer cylinder was inserted into an exposed trachea, and an inner cylinder was pulled out, retaining the outer cylinder only in the trachea.
2. After fixing each trachea by binding it with a thread, a syringe was installed.
3. The bronchial tube was washed 2 to 3 times with 600 μl of PBS. About 500 μA of BALF was collected.
ELISA was performed by the following method.
The antigen (50 μg/well) was immobilized to a microtiter plate and blocked (at 37° C. for 1.5 hours) using Block-Ace™. After a serially diluted sample was added to the microtiter plate and allowed to react, a HRP-labeled second antibody was added and reacted (with use of anti-IgG1 (×400), IgG2a (×50), and anti-IgA (×10) to allow color formation.

Figure 17:
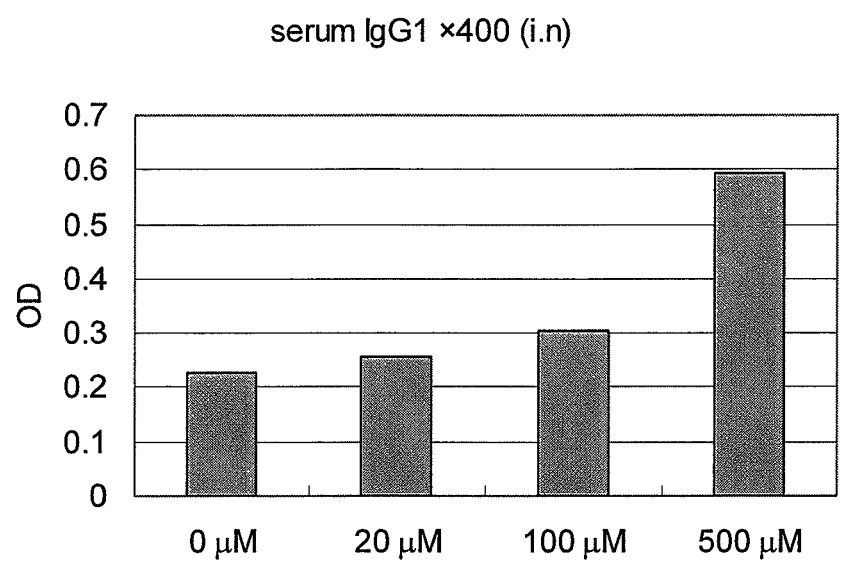
FIG. 17 is a graph showing an effect (serum IgG1) of β-hematin as a mucosal adjuvant.
Figure 18:
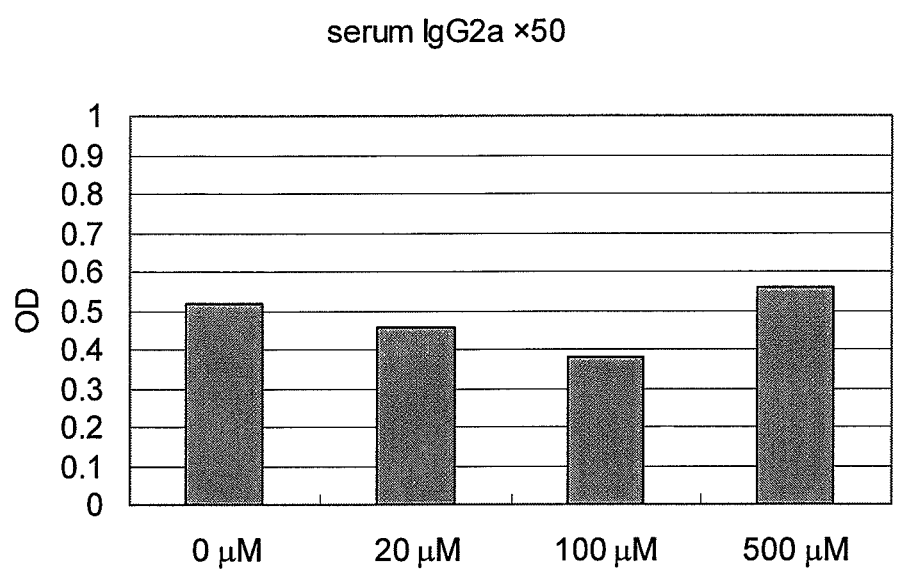
FIG. 18 is a graph showing an effect (serum IgG2a) of β-hematin as a mucosal adjuvant.
Figure 19:
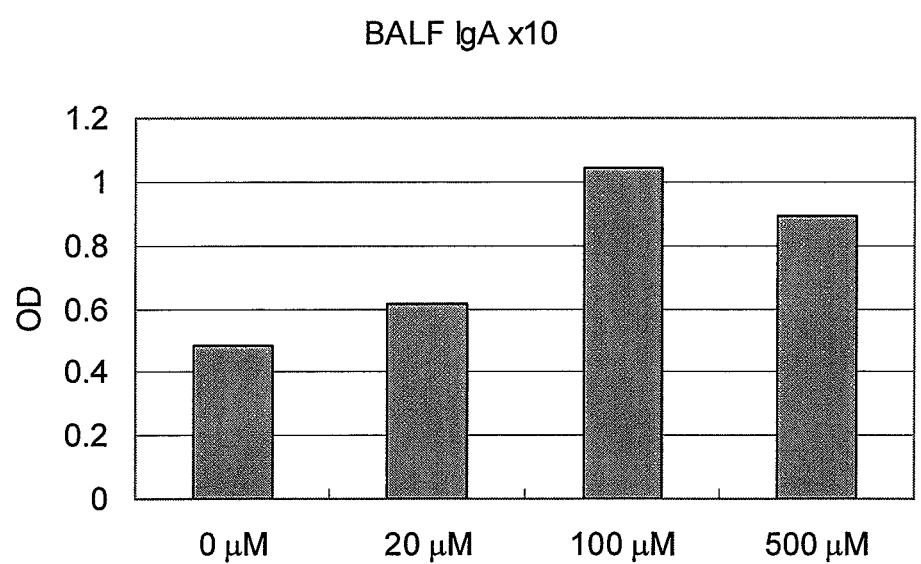
FIG. 19 is a graph showing an effect (IgA in bronchial washing fluid) of β-hematin as a mucosal adjuvant.
Figure 20:
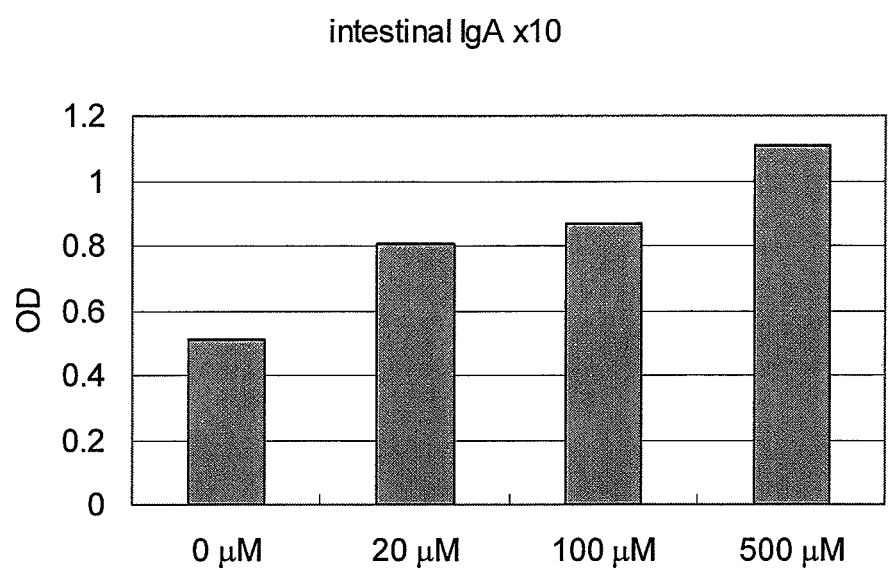
FIG. 20 is a graph showing an effect (mucosal IgA in intestinal washing fluid) of β-hematin as a mucosal adjuvant.

FIG. 17 shows serum IgA concentration one week after the third immunization; FIG. 18 shows serum IgG2a concentration one week after the third immunization; FIG. 19 shows IgA (BALF IgA) concentration in the bronchial washing fluid one week after the immunization; and FIG. 20 shows IgA concentration in the intestinal washing solution (intestinal IgA) one week after the immunization.

As shown in Figures, induction of IgG1 in the serum and IgA in the bronchus and intestinal tract was recognized in the β-hematin administration group.

INDUSTRIAL APPLICABILITY

The vaccine adjuvant composition and the vaccine composition in accordance with the present invention can be used for preventing and treating allergies and infectious diseases in animals (including humans) in the fields of medicine, veterinary medicine, and the like.

All publications, patents, and patent applications cited herein are incorporated herein as references in their entirety.

The invention claimed is:

1. A method of inducing a Th1 immunoreaction and an increase in production of IgG2 or IgG2a antibody specific to an isolated allergen or an isolated antigen in an animal, the method comprising administering to the animal, intranasally or subcutaneously, a vaccine composition comprising the isolated allergen or the isolated antigen and a vaccine adjuvant composition that comprises isolated or synthetic hemozoin or beta-hematin and Alum adjuvant.

2. The method of claim 1, wherein the vaccine composition is a mucosal vaccine.

3. The method of claim 1, wherein the hemozoin or the beta-hematin is purified.

4. The method of claim 1, wherein the antigen is selected from *Escherichia coli*, Porcine Reproductive and Respiratory Syndrome (PRRS) virus, and *Staphylococcus aureus*.

5. The method of claim 1, wherein the allergen is Derf2 of *Dermatophagoides farinae*.

6. The method of claim 1, wherein the animal is a dog or a mouse.

7. The method of claim 1, wherein the vaccine composition comprises the hemozoin or the beta-hematin at a concentration of 5 μM to 3 mM.

* * * * *